US005804449A

United States Patent [19]
Humphery-Smith

[11] Patent Number: 5,804,449
[45] Date of Patent: Sep. 8, 1998

[54] IDENTIFICATION OF HOMOLOGOUS GENE PRODUCTS ACROSS SPECIES BOUNDARIES OR OF A SINGLE SPECIES

[75] Inventor: Ian Humphery-Smith, Sydney, Australia

[73] Assignee: The University of Sydney, New South Wales, Australia

[21] Appl. No.: 809,217

[22] PCT Filed: Aug. 28, 1995

[86] PCT No.: PCT/AU95/00641

§ 371 Date: May 19, 1997

§ 102(e) Date: May 19, 1997

[87] PCT Pub. No.: WO96/10175

PCT Pub. Date: Apr. 4, 1996

[30] Foreign Application Priority Data

Sep. 28, 1994 [AU] Australia ............... PM8456

[51] Int. Cl.$^6$ ............... C07K 1/14
[52] U.S. Cl. ............... 436/63; 436/8; 530/544
[58] Field of Search ............... 436/501, 63, 64, 436/8; 530/344

[56] References Cited

U.S. PATENT DOCUMENTS

| | | | |
|---|---|---|---|
| 4,882,268 | 11/1989 | Penman et al. ............... | 435/5 |
| 4,885,236 | 12/1989 | Penman et al. ............... | 435/6 |
| 5,273,877 | 12/1993 | Fey et al. ............... | 435/6 |
| 5,547,928 | 8/1996 | Wu et al. ............... | 514/2 |

OTHER PUBLICATIONS

J. Mol. Evol. (199188), 33,379,394, G. S. Spicer, "*Molecular Evolution and Phylogeny of the Droisophila virilis Species Group as Inferred by Two dimensional Electrophoresis*".

Electrophoresis, (1994), 15, 540–543, D.P. Dean, et al., "*Spot transfer, elution and comigration with known proteins allows accurate transferral of protein identifications between distinct two–dimensional electrophoretic system*".

Electrophoresis, (1992), 13, 893–959, J. E. Celis, et al., "*The human Keratinocyte two–dimensional gel protein database- (updae 1992): towards an intergrated approach to the study of cell proliferation, differentiation and skin diseases.*", Entire Document.

"*Evolutionary biochemistry of Proteins: Homologeous and analogous proteins from avian Egg Whites, Blood Sera, Milk and other substances*", R. E. Freeney & R. G. Allison, Wiley–Interscience, New York 1969), pp. 20–23 and 125–126.

Methods in enzymology, (1993) 224, 113–121, D. Goldman and S. J. O'Brien, "*Two–dimensional Protein Electrophoresis in Phylogenetic Studies.*", Entire Document.

Electrophoresis, (1992), 13, 723–726, C. S. Baker, et al., "*A human myocardial two–dimensional electrophoresis database: Protein characteristion by microsequencing and immunoblotting.*", Entire Document.

Ann. Rev. Ecol. Syst. (1977), 8, 309–328, G. B. Johnson, "*Assessing electrophoretic similarity: The Problem of Hidden Heterogeneity*", Entire Document.

"*Clinical Chemistry: Theory, analysis and correlation*", second edition, (1989) [edited by L.A. Kaplan and A. J. Presce], The C. V. Mosby Copmpany, St. Louis, Chapter 8, Electrophoresis, J. M. Brewer, pp. 140–152. See in particular pp. 148–149 (table 8–4)).

Proc. Natl. Acad. Sci. USA, (1993), 90, 3314–3318, S.M. Hanash, et al., "*Data base analysis of protein expression patterns during T-cell ontogeny and activation.*"., Entire Document.

Zooligoical Science (1989), 6, 55–61, N. Kenmochi and K. Ogata, "*A Comparative Study of 40S Ribosomal Proteins in Artemia Salina and Rat liver: Peptide analysis by limited proteolysis and Sodium Dodecyl Sulfate Acrylamide Gel Electrophoresis.*", Entire Document.

Int. J. Biochem, (1986), 18 (12) 1073–1082, K. Han, et al., "*Sequence Homology analysis of proteins by chemical cleavages using a mono and two dimensional sodium dodecyl sulfate–polyacrylamide gel electrophoresis*", Entire Document. See in particular pp. 1073 and 1074.

Isozymes: current topics in biological and medical research, (1982), 6, 1–32, J. A. Coyne, "*Gel Electrophoresis and cryptic protein variation*", Entire Document, in particular pp. 22–23.

Proc. Natl. Acad. Sci. USA, (1987) (May), 84, 3307–3311, D. Goldman, et al., "*A molecular phylogeny of the hominoid primates as indicated by two–dimensional protein electrophoresis*", Entire Document.

J. Mol. Evol. (1988), 27, 250–260, G. S. Spicer, "*Molecular Evolution among Some Drosophilia Species Groups as indicated by Two Dimensional Electrophoresis.*", p. 253, col. 1, line 3 through col. 2, line 3, p. 256, col. 2 and p. 258, cols. 1–2.

Molec. Gen. Genet. (1973), 124, 111–128, M. Geisser, et al., "*Immunological and Electrophoretical Comparison of Ribosomal Proteins from Eight Species belonging to Entrobacteriaceae*", Entire Document, particularly pp. 117, 120 and 122.

Nature Genetics, 1993, 3: 103–112.
Mol. Pharmacol., 1992, 42: 939–46.
Gene, 1992, 114: 127–132.
Cordwell S. J., et al., Electrophoresis 1995, 16, 435–443.
Electrophorsis, 1981, 2: 135–141.
Fleischmann R. D., et al., Science, vol. 269, 496–512.
Rabilloud T., Electrophoresis 1992, 13, 429–439.
Peterson, G.L., Anal Biochem, 1977, 83, 346–356.
O'Farrell, P.H., J. Biol. Chem 1975 250, 4007–4021.

(List continued on next page.)

Primary Examiner—Toni R. Scheiner
Attorney, Agent, or Firm—Kirschstein et al.

[57] ABSTRACT

A method for determining whether a test gene product is homologous with a reference gene product produced by a cell having the same or a similar sized genome to the genome of the cell producing the test gene product. The analysis is made by step wise hierarchical comparison of $M_r$, color, level of expression and pI.

12 Claims, 7 Drawing Sheets

OTHER PUBLICATIONS

O'Farrell, P.Z., Goodman, H.M. and O'Farrell, P.H., *Cell* 1977, 12, 1133–1142.

Humphery–Smith, I., Colas des Francs–Small, C., Ambart–Bretteville, F. and Remy, R. *Electrophoresis* 1992, 13, 168–172.

Shaw, 1993 *PNAS* 90: 5138–5142.

Adams, et al., (1992) Nature, vol. 355, pp. 632–634, "*Sequence identification of 2,375 human brain genes*".

Hochstrasser, et al., (19920 Electrophoresis, 13, pp. 992–1001, "*Human liver protein map: A reference database established by microsequencing and gel comparison*".

IDENTIFICATION OF HOMOLOGOUS GENE PRODUCTS ACROSS SPECIES BOUNDARIES OR OF A SINGLE SPECIES

TECHNICAL FIELD

The present invention relates to methods for identifying homologous genes and gene products across species boundaries. The methods can also be used in comparing expression of gene products between different tissues or in different developmental stages of a single species.

BACKGROUND ART

Over the next decade and particularly the next 3–5 years, billions of dollars will be spent on sequencing the human genome and the genomes of a select number of lower organisms.

There are at present some 28 genome sequencing initiatives for mammalian species alone.

Sequencing initiatives presently expected to produce large quantities of fully sequenced genome within the next few years relate to the following species:

Mycoplasma genitalium;

Mycoplasma pneumoniae;

Escherichia coli;

Saccharomyces cerevisiae;

Caenorhabditis elegans;

Drosophila melanogaster;

Arabidopsis thaliana; and

Homo sapiens.

Already, one entire organism, Haemophilus influenzae, has been fully sequenced, (6).

The nature of life on earth means that all living organisms possess many genes in common. For example, humans share genes with slime moulds, bacteria, flies, parasites, plants, mice, sheep, cattle, cats, etc.

Within the next 5–10 years, scientists working with organisms which have not been sequenced but which are of medical, veterinary or economic importance, will be faced with a dilemma. That dilemma will be deciding how to access the mass of genetic data available for other organisms and apply it to their organism of interest.

A number of technologies exist for cross-species mapping of genes. They are unsuited to mapping large numbers of genes since they are highly labour and cost intensive, and inefficient.

The techniques that are available at present for detecting the presence of a particular gene within the genome of a different species are:

1) resequencing the genome in question. This is possibly the most efficient of the available technology, but it is extremely labour and cost intensive;

2) use of cross-species hybridisation (Southern Blot analysis). In phylogenetically removed species nucleotide sequence differences are expected between homologous genes. These can lead to negative results on Southern blots even if low stringency conditions are used. Furthermore, over the next few years the number of known genes will increase exponentially. Cross-species hybridisations for hundreds and thousands of genes would be totally impractical;

3) genes which maintain fixed chromosomal position across species boundaries with respect to anchored reference loci [for a review of the loci in mammalian species, see Reference (1)]. Anchored reference loci represent conserved homologous loci having undergone little change in different species. Linkage mapping of all genes in a given species with respect to another would not be overly productive given our present limited genetic knowledge and would also constitute a highly cost and time intensive procedure. Unfortunately these loci are probably in a minority within genomes;

4) genes which have undergone little change during speciation and show no difference in their associated post-translational modification can be recognised by the similarity in position of their gene-products on 2D electrophoresis gels (Mr and pI). However, as stated in 3) it would appear that only a small minority of genes being compared fall into this category;

5) Use of degenerate primers in polymerase chain reactions (e.g. Reference 2). This technique is far from being effective in all cases (3). Several homologous genes must have already been identified across species boundaries before the technique can be used. Again, this approach is high in cost and labour if applied to a large number of genes. This technique can be of use once a gene has been cross-species mapped several times and one wishes to extend the mapping to other species.

DESCRIPTION OF THE INVENTION

The present invention provides methods for cross-species mapping pf genes and gene products. The methods are useful in identifying the existence of homologous genes and gene products across species boundaries. They can also be applied to comparing expression of gene products between tissues within a single organism or between different developmental stages of a single organism. The methods of the invention have the potential to allow integration of existing but dissimilar protein data bases from around the world, so long as examples of gels from conflicting data bases are silver stained similarly to produce colour attributes.

Homologous genes, in accordance with the present invention, are genes which have a common origin such that they encode gene products having the same function or related functions.

Not all genes are shared amongst life forms. If those that are shared can first be identified, the task of locating novel genes within a genome becomes far simpler. Data obtained from protein microsequencing of spots associated with gene products on 2D electrophoresis gels can produce information necessary to directly access the genes involved. The genes can be accessed by oligonucleotide probing. Alternatively the genes can be identified through comparison with existing databanks or the attribution of numerical parameters, as extolled by Cordwell et al. (4).

The following attributes have been recognised as useful when matching spots on 2D electrophoresis gels. However, it is the stepwise, hierarchical analysis of these attributes, when applied to cross-species mapping of gene-products, that can lead to the identification of homologous genes. The hierarchical analysis which leads to successful cross-species mapping of homologous genes and gene products was discovered by studying the simplest of living organisms (bacteria belonging to the Class Mollicutes) and comparing them to each other and to Escherichia coli. If the initial comparisons had been made using higher organisms, the complexity of the gene products in the samples, might well have masked the analytical method that was recognised by the present inventor.

1) Similarity in Mr: Molecular mass is already the most commonly used character for comparing gene-products by one or two dimensional polyacrylamide gel electrophoresis (PAGE). On 2D electrophoresis gels the differences in molecular weight of a particular gene product across species boundaries are perhaps less pronounced than a comparison of the encoding nucleic acid sequences suggests. Although different post-translational changes in a given gene-product are likely to occur, the nature of the moieties added to proteins postranslationally means that these differences have little impact on the overall molecular weight of the gene-product as seen on 2D electrophoresis gels.

2) Similarity in colour: Colour similarity has long been recognised as useful in identifying similar spots on 2D electrophoresis gels. However, until now this feature has typically been applied to spots from samples prepared from a common source, e.g. human serum (5).

3) Similarity in level of expression as measured by integrated optical intensity of a spot. Integrated optical intensity means for organisms having similar or the same sized genomes, the relative percentage of optical intensity associated with a spot with respect to the total optical intensity associated with all the spots visible on a gel, or within a gel image database; or the absolute intensity of the spot for organisms having significant differences in genome size. Use of this attribute assumes that a given gene-product will have a similar level of relative functional importance to the host cells being compared. This is not true for all gene products but is true for a large percentage of "housekeeping" genes essential for maintaining life.

The degree of phylogenic closeness between the organisms being compared should provide a measure of the percentage of gene-products which should be expressed at similar levels with respect to the total output of the genome under study. This matching character has potential to significantly limit the application of the method of the invention in identifying homologous gene-products. That is it is only applicable to spots that do not undergo large changes in their relative levels of expression, across species boundaries. However, the method has been found to be useful for a large percentage of spots visible on gels.

4) Similarity in isoelectric point, pI: pI is an inherent characteristic of proteinaceous gene-products. However, it has been found to be a less reliable attribute than 1), 2), or 3) for cross-species mapping. This is probably because different post-translational changes take place when homologous genes are expressed in different species or organ systems. However, where similarity is identified for this attribute, it is highly indicative of cross-species homology. A good example of the extent of variation in pI observed in an homologous gene-product across species boundaries is that of phosphoglycerate kinase, which, from data preened from Genbank has a pI ranging from 4.8 pH in *Escherichia coli* through to 7.9 pH in humans.

These attributes can be analysed using individual gels or databases representative of a series of gels.

According to a first aspect of the present invention there is provided a method for determining whether a test gene product is homologous with a reference gene product produced by a cell having the same or a similar sized genome to the genome of the cell producing the test gene product, which method comprises:

1) comparing the Mr of the test gene product with the $M_r$ of the reference gene product, 2) if the $M_r$ of the test gene product differs from the $M_r$ of the reference gene product by not more than the greater of 10 kD or 10% of the $M_r$ of the reference gene product, comparing the silver stained colour of the test gene product with the silver stained colour of the reference gene product, 3) if the silver stained colour of the test gene product is within 20% of shade units of the colour of the reference gene product, comparing the level of expression of the test gene product with the level of expression of the reference gene product, 4) if the relative level of expression of the test gene product differs from the relative level of expression of the reference gene product with respect to the total optical intensity associated with all the spots detected within a gel by not more than 15%, comparing the pI of the test gene product with the pI of the reference gene product;

5) determining whether the pI of the test gene product differs from the pI of the reference gene product by not more than 4 pH units, and if all of the criteria specified at steps 2 to 5 are met, determining that the gene products are homologous.

Similarity of genome size is measured considering the actual size of the genomes in question. For organisms with small genomes e.g. the Mollicutes having genome sizes ranging from 600–1700 kb, 50% variation, (variation of the order of 500,000 bp) is allowable for genomes to be still considered similar in size. By contrast, amongst vertebrates, which have much larger genomes, 20–25% variation would be considered the maximum variation for genomes to be considered similar in size.

According to a second aspect of the present invention there is provided a method for determining whether a test gene product is homologous with a reference gene product produced by an organism having a genome which differs significantly in size from the size of the genome of the organism producing the test gene product, which method comprises:

1) comparing the $M_r$ of the test gene product with the $M_r$ of the reference gene product, 2) if the $M_r$ of the test gene product differs from the $M_r$ of the reference gene product by not more than the greater of 10 kD or 10% of the $M_r$ of the reference gene product, comparing the silver stained colour of the test gene product with the silver stained colour of the reference gene product, 3) if the silver stained colour of the test gene product is within 20% of shade units of the colour of the reference gene product, comparing the level of expression of the test gene product with the level of expression of the reference gene product, 4) if the absolute level of expression of the test gene product differs from the absolute level of expression of the reference gene product by not more than 40%, comparing the pI of the test gene product with the pI of the reference gene product;

5) determining whether the pI of the test gene product differs from the pI of the reference gene product by not more than 4 pH units, and if all the criteria specified at steps 2) to 4) are met, determining that the test gene product is homologous to the reference gene product.

The $M_r$ of the gene products is typically determined by 2D gel electrophoresis with respect to a series of molecular weight standards.

The methods of the invention rely upon colour based analyses of 2D images. The colour in silver stained gels depends upon the specific binding of silver ions to amino acid residues. The ratio of amino acids in each protein defines the final colour of a given protein spot. Shaw (13) has already demonstrated the utility of relative amino acid composition for use in protein characterisation.

It will also be understood that alternatives to silver stained colour such as fluorescence, chemiluminescence or colour-producing dye could be employed in this second comparative step. With these systems similar gene products will generate values +/−20% of the relevant scale employed in their comparison.

While colour can be judged by eye, typically, colour with respect to a colour standard can be assigned to silver stained gene products using a range of 24 Bit HSI (Hue Saturation Intensity) or RGB (Red Green Blue) or times three 8 Bit colour via a charge coupled device and a video acquired image. In that case, similar coloured gene products will have colours +/−20% of the colour scale employed to measure spots.

With a colour sensitive device thousands of colour shade units could be employed. Quantitative densitometry is restricted to the use of monochromatic light. However, colour attributes can be assessed following more traditional approaches to densitometry. In this process existing software is used for image handling and comparisons for quantitive densitometry followed by image reacquisition using colour attributes with respect to a colour standard. For example, creation of an 8 Bit black and white image, as opposed to the alternate 24 Bit image file which would later be given over to colour acquisition.

Typically, silver staining is performed using long protocols as reviewed by Rabilloud (7).

Typically, levels of expression can be compared by measuring optical intensity or density for individual spots visualised by 2D gel electrophoresis.

Levels of expression can also be compared using pseudo-colour imaging of 2D gels, where the optical intensity of spots is graded into categories and attributed pseudocolour rather than being measured in ppm.

For example, using four categories, the intensities of spots can be assigned intensity levels of green, yellow, red and blue where these are in an order of decreasing optical intensity. Similar levels of expression then refer to dots of the same colour.

Not all spots or silver stained gene products have equal levels of optical intensity or size. Both features contribute to absolute and relative optical intensity. Spot size is as important as optical intensity, and a significant difference in size can lead a potential match on optical intensity to be discarded.

Because of the hierarchical nature of the analysis less variability is expected for $M_r$, while greater variability is expected for pI.

Close similarity or identical values obtained for matches of any or all of the four attributes used in detecting homology can be considered to be highly suggestive of homology. However, it is the stepwise application of the four attributes that provides a useful technique for detecting potential homologues by reducing the number of possible matches to a manageable number.

It is expected that as phylogenetic distance is reduced between the organisms or tissue types being compared, then so too will the disparity between the attributes being compared. The reverse would apply to distantly related species, e.g. horses and monkeys or bacteria and protozoans, where considerable differences could be expected between homologous gene-products visible on 2D gels.

To date, the method has been conducted in a semi-automated fashion. However, the methods can be totally automated using current technological expertise being applied to image analysis of 2D electrophoresis gels.

In its simplest form, automation would involve the use of a sliding scale on a computer screen to select minimum and maximum values for each of the four attributes being compared. These values then represent the parameters for searching the database of the gel or gels being compared to the reference or starting point gel, i.e. something is being compared with something else. Therefore, one is called the 'reference' to which the comparison is being made. Lower and higher molecular weights do not necessarily use the same percentages or absolute values for their respective degrees of freedom for attributing similarity, thus, search parameters can require mathematical calculation. As more experience is gained searching databases, potentially more elaborate matrices can be developed to handle the stepwise analysis of databases. In addition, the use of some sort weighting of attributes can be envisaged so that once parameters being compared are nearly identical they can be given a high score.

Using the methods of the present invention with complex species has the potential to generate a number of possible matches with a given reference gene-product. This is still a significant achievement in mapping complex species. Protein microsequencing or microanalysis can then be used to discern which of the putative positives are indeed homologous. As the number of entries in centralised gene and protein databases increases, then so too will the ability of additional parameters (for example, amino acid composition, peptide mass fingerprinting, protein microsequnce, etc.) to be able to reduce confusion or eliminate altogether the occurrence of more than one possible match within the 2D gel image being compared.

The method of the invention can be further improved if a set of approximately ten randomly situated Mr/pI markers is co-migrated within the species being compared to provide known tie-in points within gels being matched. At present we have used horizontally placed carbamylation ladders and vertically distributed Mr standards. The method becomes more efficient if a set of standards not restricted to one X and one Y axis is used.

The methods of the invention are likely to represent savings in the order of person-years in the molecular laboratory when investigators are faced with the task coming to grips with the molecular complexity of a poorly defined organism.

Substitutions and deletions at the level of nucleic acid or amino acid residue sequence are less likely to interfere with the correct identification of an homologous gene-product by the methods of the invention in contrast to other currently available technologies.

BRIEF DESCRIPTION OF TEE DRAWINGS

FIG. 1 shows an example of a polypeptide map (gene-product map) of a bacterium, *Spiroplasma melliferum*.

This is a data base constructed from many 2D electrophoresis gels [y axis=$M_r$; x axis=isoelectric point relative to carbamylation standards of GAPDH (glyceraldehyde-3-phosphate dehydrogenase]. It provides an example of measuring $M_r$ and pI for use in the crossspecies mapping methods of the invention.

FIGS. 2a and b each shows a silver stained gel marked to indicate variation in spot colour as detected by silver staining of proteins and as revealed in a full colour photograph of the gel.

Figure 6A:
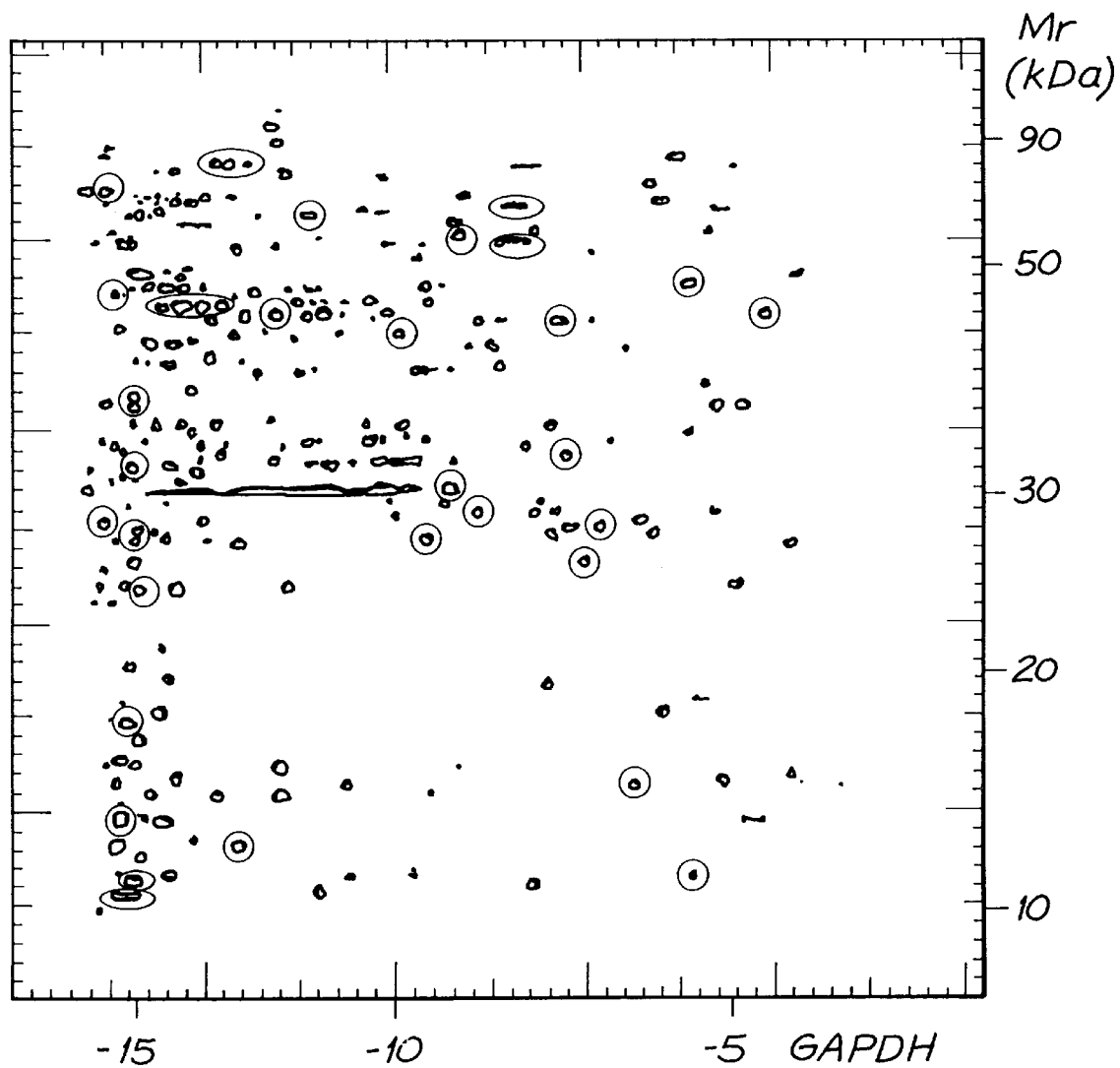
Figure 6B:
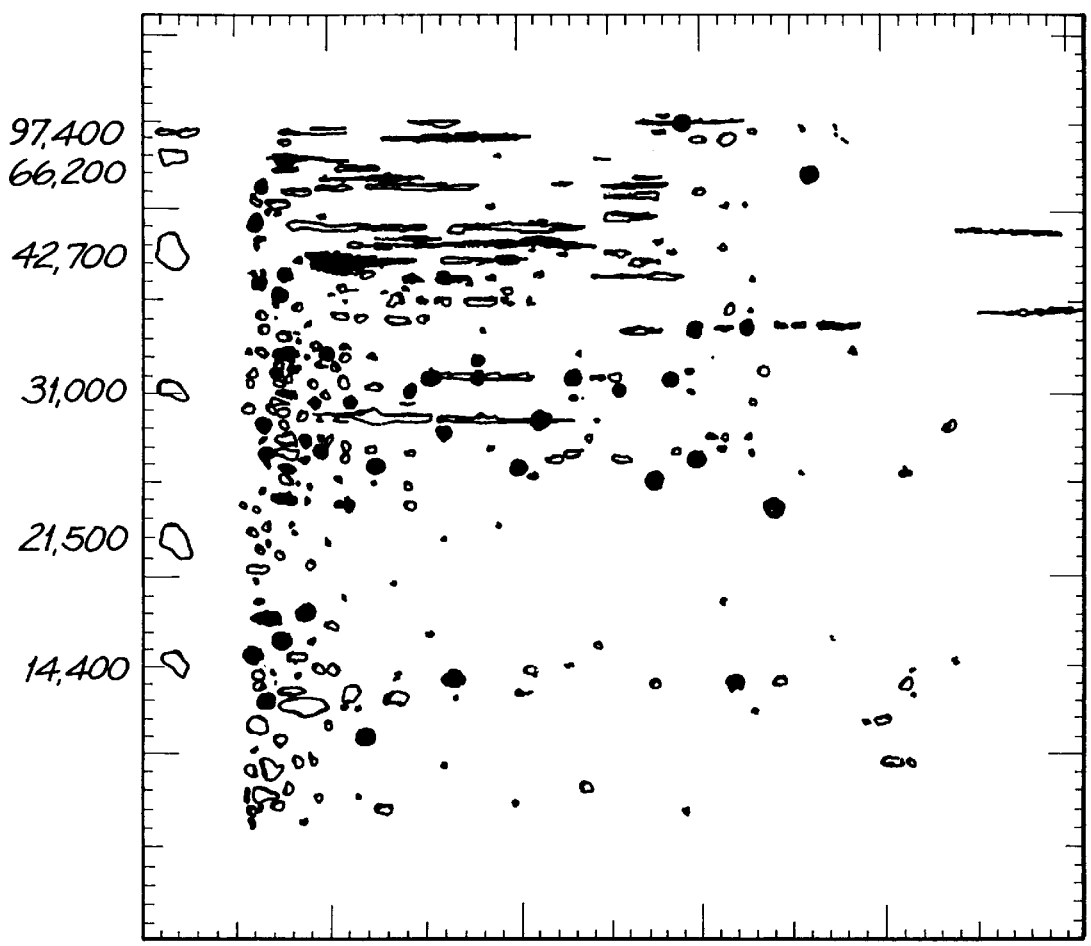

FIG. 6 shows spot maps of *Spiroplasma taiwanense* indicating homologous gene products whereby: a) 31 open circles represent homology with *S. melliferum* and *S. sabaudiense*; and b) 66 solid spots outline homologies with *Escherichia coli* type K-12 prototroph strain W3110. N.B. In b) ampholyte mixtures have been optimised to increase comparative resolution and thus higher molecular weight proteins are less well focused. The use of IPG-DALT technology can avoid these shortcomings. The preliminary nature of these results would suggest that many more homologies await detection. Larger format second dimension gels (200×230 mm), the use of IPG-DALT technology and automated analysis are likely to greatly increase the number of homologies detected.

BEST METHOD OF PERFORMING THE INVENTION
Materials Silver staining solutions

Fixing solution
    400 mL ethanol
    100 mL acetic acid
    Make up to 1.0 L with distilled water
    60 min.
Incubation solution **
    75 mL ethanol
    17.0 g sodium acetate×3H$_2$O
    1.3 mL glutardialdehyde (25% w/v) *
    0.50 g sodium thiosulfate, Na$_2$S$_2$O$_3$×5H$_2$O
    Make up to 250 mL with distilled water
    16 hours (Overnight)
Washing
    ×3 rinses in distilled water for 5 min.
Silver solution **
    0.25 g silver nitrate ***
    50 µl formaldehyde *
    Make up to 250 mL with distilled water
    40 min.
Rinse
    ×1 in distilled water for 5 min.
Developing Solution **
    6.25 g sodium carbonate
    25 µl formaldehyde *
    Make up to 250 mL with distilled water 10 min (XL)/60 min (2D)
    60 min
Stop solution
    1.2 g EDTA-Na×2H$_2$O
    Make up to 250 mL with distilled water.
* Note: Add these components immediately before use.
** Use disposable plastic containers for preparation of these solutions and use them only once.
*** Weigh using gloves and throw them away immediately. Do not use the same gloves when handling gels.
N.B. Handle gels only in region of gel beyond the migration front.
N.B. Formaldehyde must be fresh.

Sample preparation:

Bacteria were harvested in exponential growth phase after growth at 28° C. in 1l of Leibovitz's L-15 medium supplemented with 10% Foetal Calf Serum, 10% Tryptose Phosphate Broth and 1% L-Glutamine which had been filtered (0.2 µm) to remove sediment. The stock solution was then concentrated by centrifugation at 9,000 g at 4° C. and washed thrice in the following buffer solution in deionised water at 4° C.: 3.0 mM KCl; 1.5 mM KH$_2$PO$_4$; 68 mM NaCl and 9.0 mM NaH$_2$PO$_4$. Following rinsing, excess buffer was removed by inversion and tapping of the centrifuge tube for 30 sec. prior to resuspension of the sediment in 8–10 volumes of Lysis Buffer: 2% Triton X-100; 2% β-mercaptoethanol; 2% ampholyte solution pH 3–10 (Millipore Corp., Bedford, Mass.); 9M Urea and 8 mM PMSF. This solution was then snap frozen at −70° C. and thawed once before undergoing four cycles of 5 min on ice and 1 min bead-beating (Mini-Bead-Beater, Biospec Product, UK) in the presence of 0.5 g of 0.1 mm zirconium beads. Sample heating during bead-beating was less than 1° C./min. The homogenised sample was recovered from the beads and beads washed twice with 4 volumes of Lysis Buffer. The sample was then centrifuged at 30,000 g for 45 min at 4° C. to remove any non-solubilised material, aliquoted and stored at −20° C. until use. Sample dilutions were carried out in the following buffer solution: 2% β-mercaptoethanol; 2% ampholyte solution pH 3–10 (as for Lysis Buffer); 0.5% Triton X-100; 8M Urea and 0.05% Bromophenol Blue. Protein concentration was determined using a Sigma Protein Assay Kit (St. Louis, Mo.) based on a modification of the Lowry method (8) and calculated from the average of triplicate serial dilutions of the sample with respect to known standards for which optical density was also triplicated.

Figure 1:
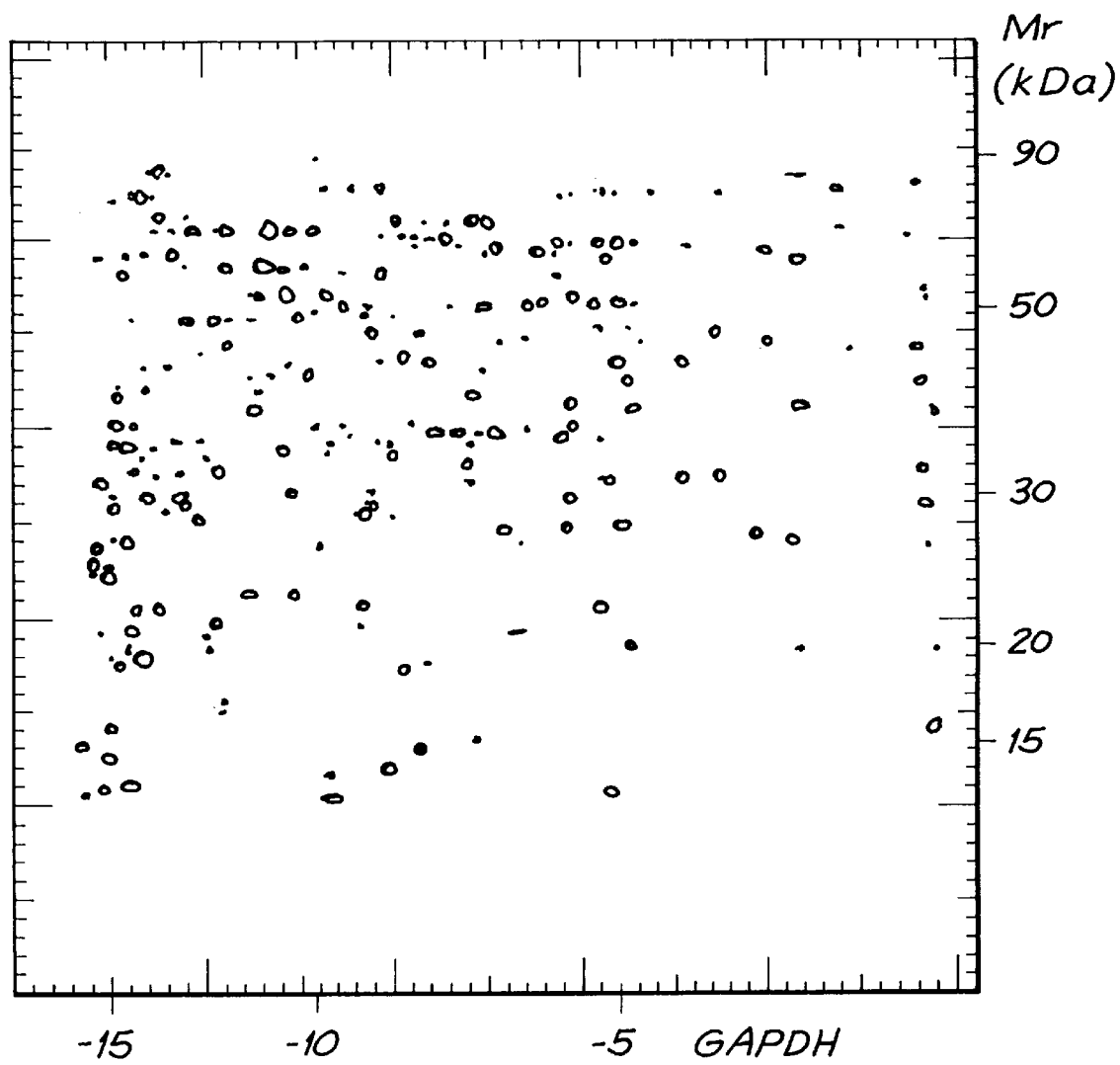
Figure 2A:
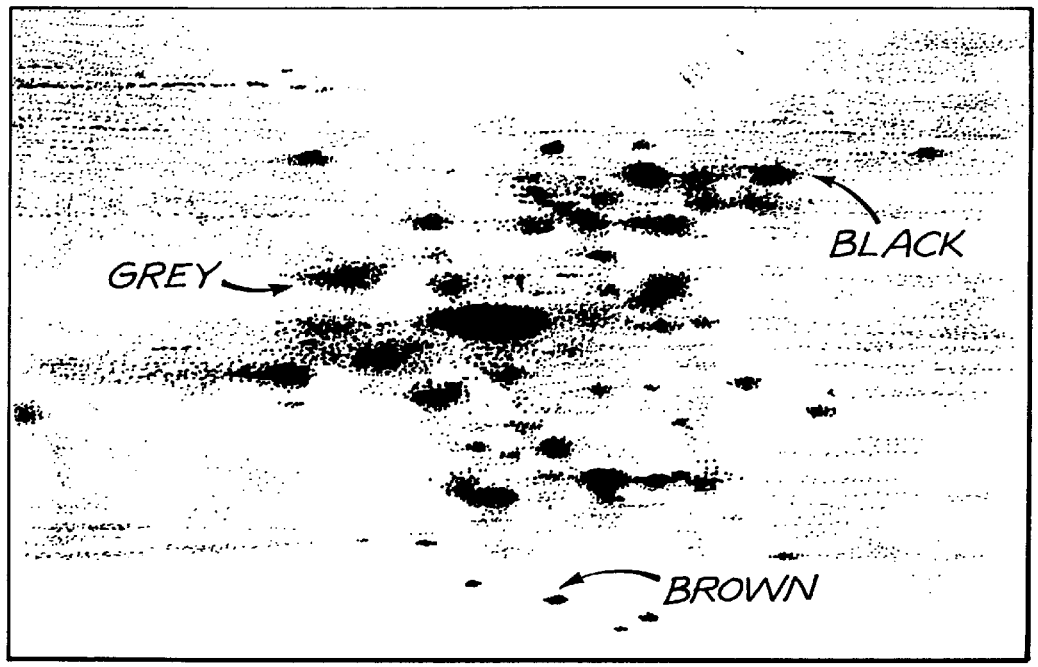
Figure 2B:
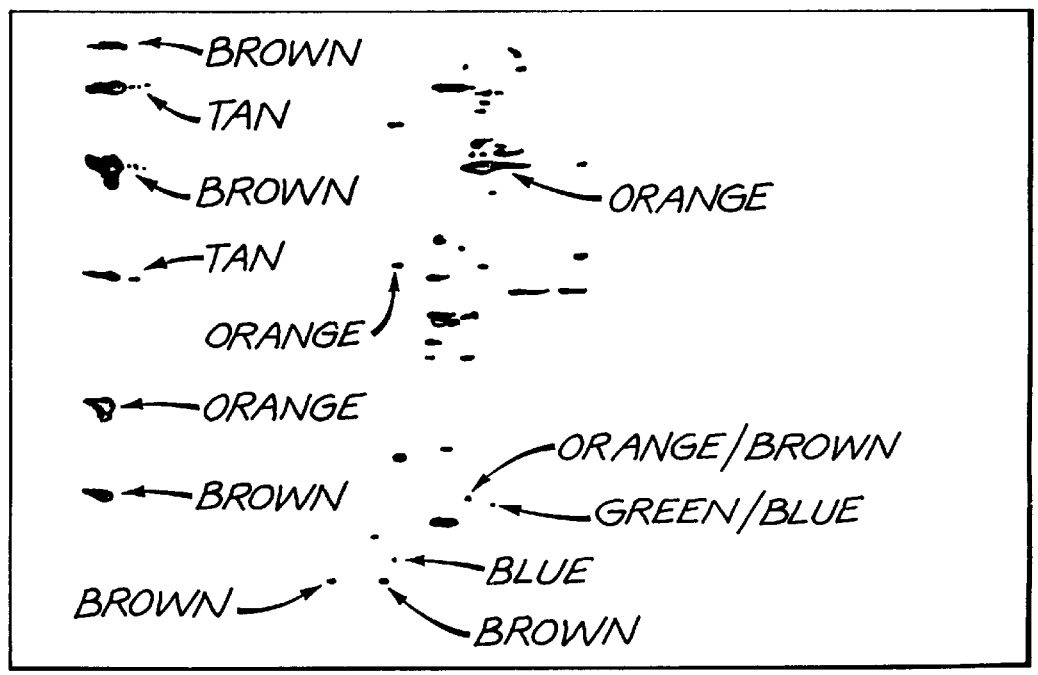
Figure 3:
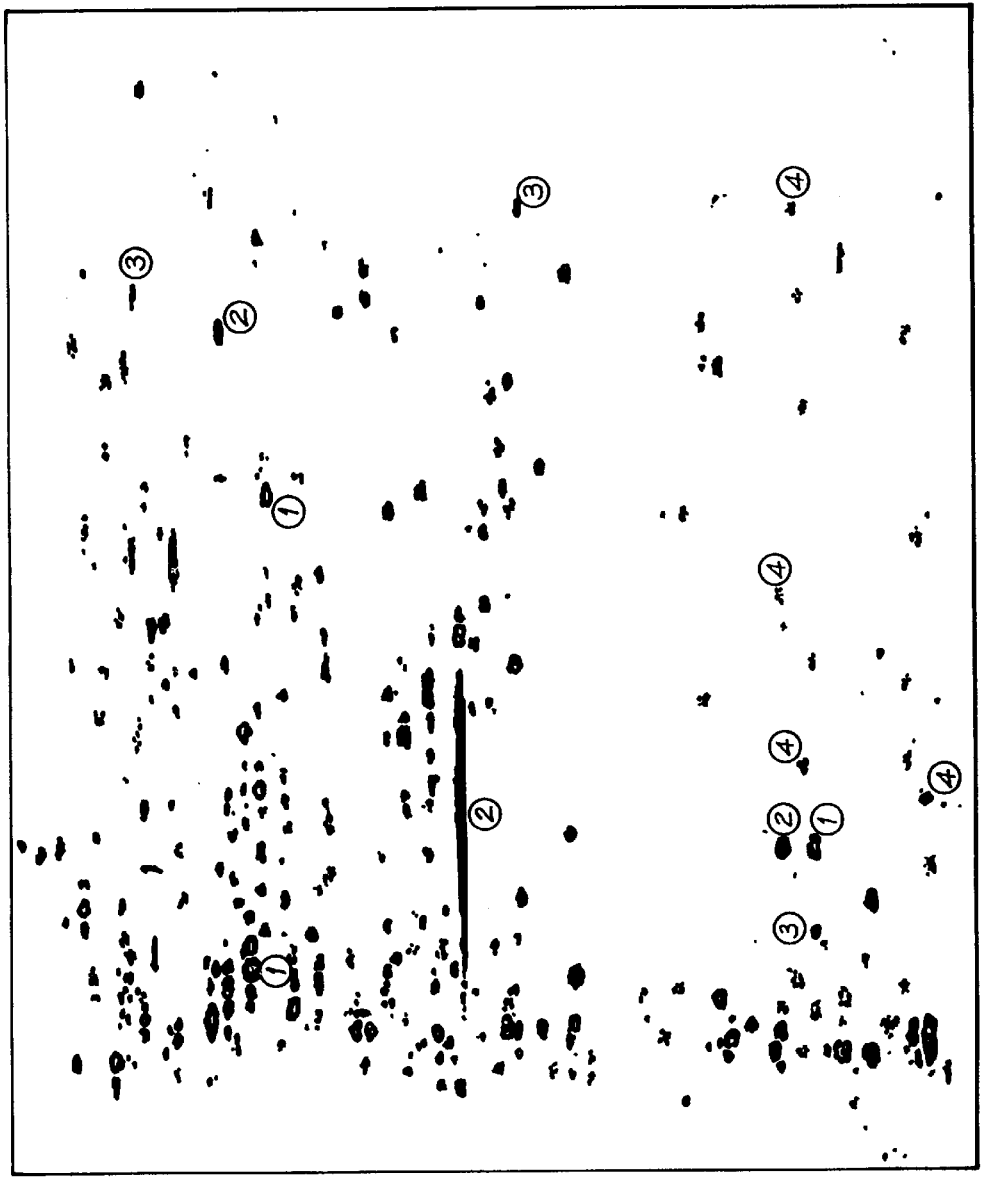
FIG. 3 shows a black and white copy of a pseudo-colour image showing the relative level of expression for each of 263 gene-products expressed in descending order of green >yellow>red>blue. On the figure green=1, yellow=2, red=3, blue=4.
Figure 4:
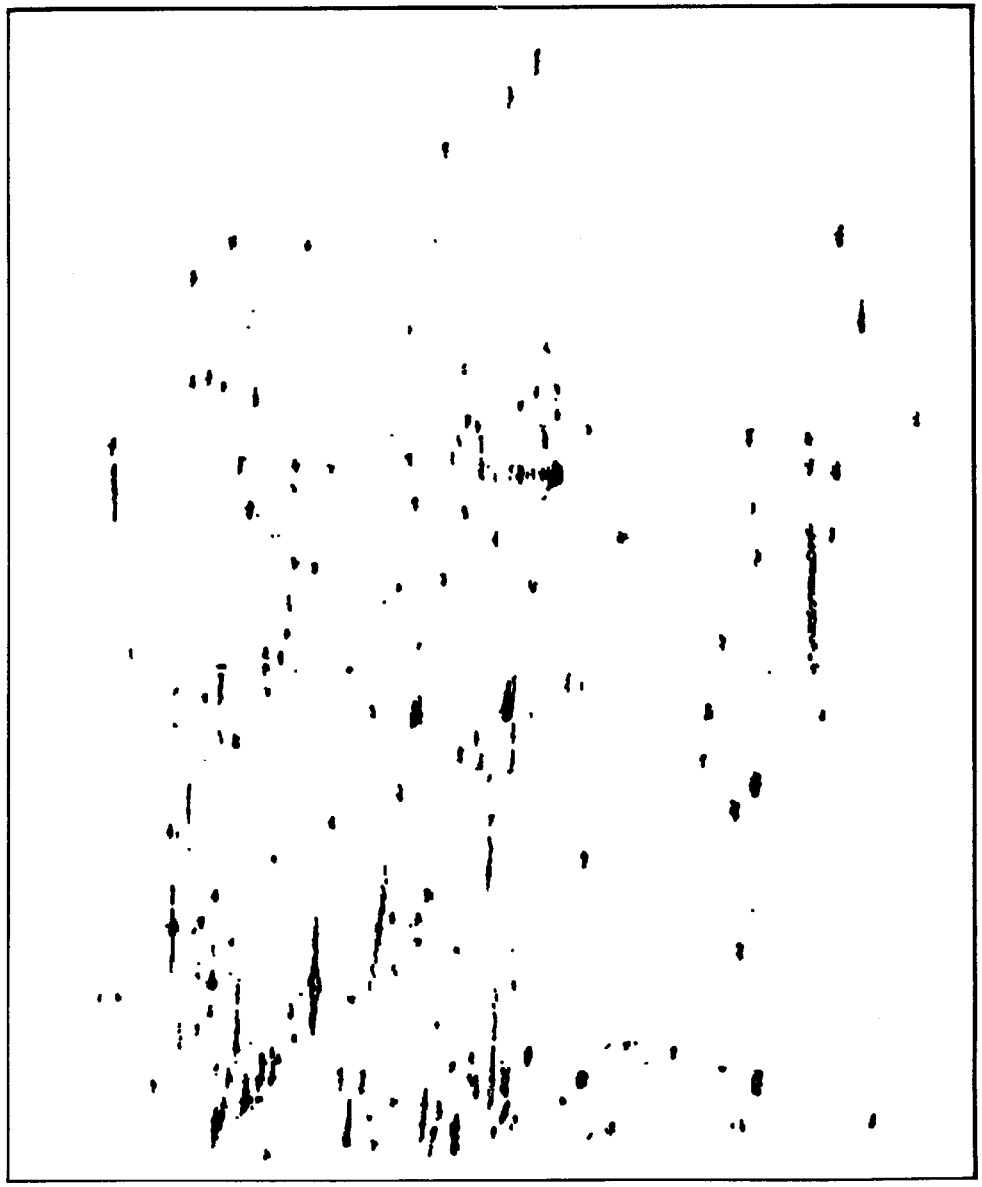
FIG. 4 shows a black and white copy of a 2D electrophoresis gel demonstrating that not all protein spots of silver stained gene-products have equal levels of expression as measured by normalised optical spot intensity and synthetically colour coded for green>yellow>red>blue.
Figure 5:
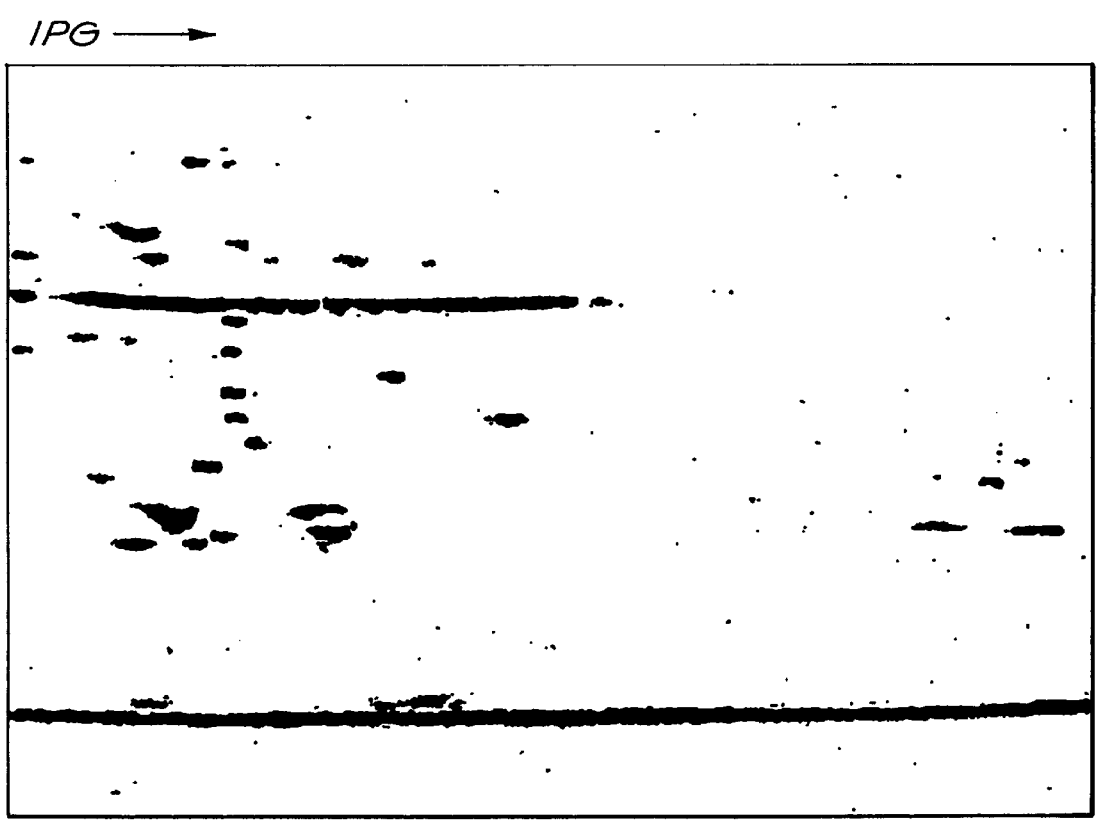
FIG. 5 shows an IPG-DALT gel revealing the entire GAPDH ladder.

Two-Dimensional Gel Electrophoresis (2DGE):

2DGE was conducted following four variations of the original O'Farrell (9) method (see below IPG-DALT (a) & (b), ISO-DALT and NEPHGE, all of which are equally adaptable to the present technology for cross-species mapping). All gels were silver stained using the technique of Heukeshoven and Dernick (10) except that incubation was extended to 16h. Isoelectric points were expressed relative to GAPDH carbamylation standards (Pharmacia, Uppsala, Sweden). These standards were allocated positions with respect to the entire GAPDH 'ladder' as visualised in IPG-DALT gels (FIG. 5). GAPDH was chosen because of the relative paucity of polypeptides in the 36,000 Daltons molecular mass region of *S. taiwanense*. Molecular mass was calculated from standards obtained from Pharmacia (Uppsala, Sweden). Polypeptide position relative to standards was calculated from two or three additional gels including pI and Mr standards for each 2D technique which had been matched and normalised by computerised image analysis (CIA).

a) IPG-DALT (Excel Gel; T: 8–18% )

IPG-DALT electrophoresis was carried out following the manufacturer's instructions using 11 cm Immobiline Dry Strips pH range 3.0–10.5 in the first dimension and Excel Gel SDS, gradient 8–18% in the second dimension (Pharmacia, Uppsala Sweden). Samples containing 15 µg of protein were loaded onto Immobiline strips and focused during 22500 V/H for 3h at 300 V, 8h at 700 V and the remaining time at 2000 V. Preliminary experiments found sample concentrations of 15 µg to maximise both resolution and spot number.

b) IPG-DALT (SDS-PAGE; T: 15%)

The above procedure was replicated except that in the second dimension, SDS polyacrylamide gels were produced in our laboratory: Running gel T=15% and C=2.6%; Stacking gel T=4% and C=2.6%. Here, sample concentration was increased to 100 μg (4 gels) and 150 μg (3 gels) of protein and the second dimension was run in a Protean II electrophoresis tank (Biorad, Richmond, Calif.) until the migration front had migrated 14 cm at limiting power of 1 Watt (Stacking gel) and 5 Watts (Running gel) per electrophoresis plate in Tris/Glycine/SDS Running Buffer Miligene (Bedford, Mass.).

c) ISO-DALT

For the ISO-DALT procedure, samples containing 100 μg of protein were focused during 22000 V/H for 3h at 300 V, 17h at 700 V and the remaining time at 3000 V in glass tubes (1.2 mm diameter) which produced 13 cm long gels (T=9.6%, C=12%). Ampholytes used were pH 2.5–5 and pH 5–8 (Pharmacia, Uppsala) and pH 3–10 (Millipore Corp., Bedford, Mass.) mixed in a ratio to maximise resolution across species boundaries rather than for just one species. Square format gels were then produced in the second dimension as described above for the IPG-DALT (SDS-PAGE) technique.

d) NEPHGE

NEPHGE was conducted following the protocol described for the ISO-DALT technique, except the first dimension was run during only 3750 V/H for 1h at 400 V and the remaining time at 800 V and the current, anode and cathode buffers were reversed as described by O'Farrell (11). The ampholyte mixture used was pH 3–10 (Millipore Corp., Bedford, Mass.) and pH 8–10 (Pharmacia, Uppsala) in the ratio 4:1.

Computerised Image Analysis:

CIA was carried out as described previously (12) using a Gemini Image Analyser (Applied Imaging, Newcastle, UK). Following construction of non-real composite reference gel images from a series of gels representative of each 2D electrophoretic technique, nonreplicated spots were removed from databases prior to quantitative comparisons. All polypeptide maps are figured within a plot frame comprised of 512×512 pixels.

Cross-species mapping (CSM):

CSM was based upon information produced by two-dimensional gel electrophoresis of *Spiroplasma taiwanense, S. sabaudiense, S. melliferum, Mycoplasma genitalium* and *M. pneumoniae* (five Mollicutes species of bacteria) and K12 type prototroph *Escherichia coli* strain W3110 as used in the *E. coli* gene-protein database (University of Michigan). Initially and following paired migration (same electrophoresis run for both 1D and 2D) of two organisms being compared in the presence of carbamylated GAPDH isoelectric point standards and molecular mass markers, gels underwent ultrasensitive silver staining by an improved version of that described by Heukeshoven & Dernick (10). Additional polypeptide databases using CIA were constructed from 8–10 good quality gels of each organism being compared using ampholyte mixtures designed to maximise comparative resolution. The use of IPG-DALT gels avoids the need to optimise ampholyte mixtures during cross-species mapping of gene-products. Cross-species matches were determined by the hierarchical application of $M_r$ similarity, colour similarity, expression level comparison and pI comparison. Determined matches were then transferred to reference databases for each species. The latter approach should become redundant once the cross-species matching has been entirely automated. Some 95 homologies across species boundaries for *Spiroplasma taiwanense* with respect to *E. coli* were identified. More recently, some of these findings relating to cross species matches between Mollicute species have been confirmed using protein microsequencing, amino acid composition and peptide-mass fingerprinting. Results are shown in FIG. 6. The following matches have been confirmed between *Spiroplasma taiwanense, Spiroplasma melliferum, Mycoplasma genitalium* and *M. Dneumoniae*: dna K, elongation factor Tu, elongation factor Ts, phosphopyruvate hydratase; phosphoglycerate kinase, GroEL, GroES, and a number of ribosomal proteins.

INDUSTRIAL APPLICABILITY

The methods of the invention can be used in:

a) Cross-species identification of homologous gene-products visible on silver stained 2D electrophoresis gels. If 2D maps are already available for a molecularly well-defined species, then the gene-products can be given putative homology status with a good degree of certainty. Equally useful is the ability to say for certain that a gene is present in different organisms, especially when one of the samples being compared is molecularly well defined.

b) Identifying homologous gene-products between different organ systems within the same organism, e.g. in humans between liver, lungs, heart and brain or in plants between stems, roots and leaves.

c) Reducing the error rate as applied to spot matching of silver stained 2D electrophoresis gels where colour variation is apparent. Many staining techniques applied to resolve spots on 2D electrophoresis gels, blots or photographic and radiographic images of gels do not manifest colour differences and cannot therefore utilise the above technology. However, a variety of dyes or stains such as fluorescence, chemiluminescence or colour producing dyes could also be analysed by the present invention.

The cross-species mapping methods of the invention make it possible to take molecularly poorly defined material (be it associated with biological specimens of medical, veterinary, agricultural or biotechnological importance) and short-cut the need to resequence entire genomes for every biological system of interest. Molecularly understudied organisms and tissues can rapidly be transformed (possibly within weeks leading up to just one morning's work, ie. computer based comparisons of appropriate prepared samples) into molecularly well defined material, thereby economising in time and cost. In the next 18–24 months, the scientific community will have access to what constitutes total genomic sequence for *Haemophilus influenzae, Mycoplasma genitalium, Mycoplasma pneumoniae, Escherichia coli* and *Saccharomyces cerevisiae*. Others will then follow. Well defined protein maps produced from 2DGE (gene-product maps) will then provide the necessary resource by which information can be rapidly and cost effectively preened.

This technology can be applied to analysis of disease causing micro-organisms (prokaryotes) of plants, humans and domestic animals, leading to vaccine preparations based on an overall understanding of antigenic constituents (both immunogenic and protective), drug targetting and design based on vulnerable molecules elucidated within a given system and selection of highly specific markers for use in disease diagnosis. Once *Caenorhabditis elegans* has been sequenced, this information can be applied to eukaryotic disease causing organisms, causing disease such as malaria, sleeping sickness and schistosomiasis in humans; and helminth infections of plants and animals. The latter are all presently the target of innumerable prophylactic and control efforts conducted by many of the world's leading pharmaceutical companies. The analysis of human tissues and disease states, including cancers, can then follow. The ability of this technology to follow multigenic phenomena and help in characterising the genes involved will find application in better understanding carcinogenesis and eventually cancer treatment and prophylaxis.

REFERENCES (1) Nature Genetics, 1993, 3: 103–112

(2) Mol. Pharmacol., 1992, 42: 939–46

(3) Gene, 1992, 114: 127–132

(4) Cordwell S. J. et al., Electrophoresis 1995, 16, 438–443

(5) Electrophoresis, 1981, 2: 135–141

(6) Fleischmann R. D. et al., Science, Vol. 269, 496–512

(7) Rabilloud T., Electrophoresis 1992, 13, 429–439.

(8) Peterson, G. L., Anal. Biochem. 1977, 83, 346–356.

(9) O'Farrell, P. H., J. Biol. Chem. 1975, 250, 4007–4021.

(10) Heukeshoven, J. and Dernick, R., in: Radola, B. J. (Ed.), Elektrophorese Forum '86, Technische Universität München, München, pp 22–27.

(11) O'Farrell, P. Z., Goodman, H. M. and O'Farrell, P. H., Cell 1977, 12, 1133–1142.

(12) Humphery-Smith, I., Colas des Francs-Small, C., Ambart-Bretteville, F. and Remy, R Electrophoresis 1992, 13, 168–172.

(13) Shaw, 1993 PNAS 90: 5138–5142

I claim:

1. A method for determining whether a test gene product is homologous with a reference gene product produced by a cell having the same or a similar sized genome to the genome of the cell producing the test gene product, which method comprises the steps of:

1) comparing the $M_r$ of the test gene product with the $M_r$ of the reference gene product, 2) if the $M_r$ of the test gene product differs from the $M_r$ of the reference gene product by not more than the greater of 10 kD or 10% of the $M_r$ of the reference gene product, comparing the silver stained colour of the test gene product with the silver stained colour of the reference gene product, 3) if the silver stained colour of the test gene product is within 20% of shade units of the colour of the reference gene product, comparing the level of expression of the test gene product with the level of expression of the reference gene product, 4) if the relative level of expression of the test gene product differs from the relative level of expression of the reference gene product with respect to the total optical intensity associated with all the spots detected within a gel by not more than 15%, comparing the pI of the test gene product with the pI of the reference gene product;

5) determining whether the pI of the test gene product differs from the pI of the reference gene product by not more than 4 pH units, and if all of the criteria specified at steps 2 to 5 are met, determining that the gene products are homologous.

2. A method for determining whether a test gene product is homologous with a reference gene product produced by an organism having a genome which differs significantly in size from the size of the genome of the organism producing the test gene product, which method comprises the steps of:

1) comparing the $M_r$ of the test gene product with the $M_r$ of the reference gene product, 2) if the $M_r$ of the test gene product differs from the $M_r$ of the reference gene product by not more than the greater of 10 kD or 10% of the $M_r$ of the reference gene product, comparing the silver stained colour of the test gene product with the silver stained colour of the reference gene product, 3) if the silver stained colour of the test gene product is within 20% of shade units of the colour of the reference gene product, comparing the level of expression of the test gene product with the level of expression of the reference gene product, 4) if the absolute level of expression of the test gene product differs from the absolute level of expression of the reference gene product by not more than 40%, comparing the pI of the test gene product with the pI of the reference gene product;

5) determining whether the pI of the test gene product differs from the pI of the reference gene product by not more than 4 pH units, and if all the criteria specified at steps 2) to 4) are met, determining that the test gene product is homologous to the reference gene product.

3. A method according to claim 1 or claim 2 wherein the $M_r$ of the gene products is determined by 2D gel electrophoresis with respect to a series of molecular weight standards.

4. A method according to claim 1 or claim 2 wherein colour with respect to a colour standard is assigned to silver stained gene products using a range of 24 Bit HSI, or RGB, or times three 8 Bit colour via a charge coupled device and a video acquired image.

5. A method according to claim 1 or claim 2 wherein colour is measured using a colour sensitive densitometric device.

6. A method according to claim 1 or claim 2 wherein levels of expression are compared by measuring optical intensity or density for individual spots visualised by 2D gel electrophoresis.

7. A method according to claim 1 or claim 2 wherein levels of expression are compared using pseudocolour imaging of 2D gels, the optical intensity of spots being graded into categories and attributed pseudo colour rather than being measured in ppm.

8. A method according to claim 1 or claim 2 which is semi-automated or totally automated.

9. A method of comparing expression of a gene product in different tissues or different development stages of an organism which method comprises assessing homology of the gene product between the tissues or development stages by the method according to claim 1.

10. A method according to claim 1 or claim 2 wherein a set of about ten randomly situated $M_r$/pI markers is comigrated within the species being compared to provide known tie-in points with gels being matched.

11. The method according to claim 10 wherein the markers are not restricted to one X and one Y axis.

12. A method according to claim 1 or claim 2 wherein a fluorescence, chemiluminescence or colour producing dye or stain is used in place of silver stained colour for colour comparison of the test and reference gene products and wherein homologous gene products have values of +/−20% of a relevant scale employed in their comparison.

* * * * *